Figure 1:
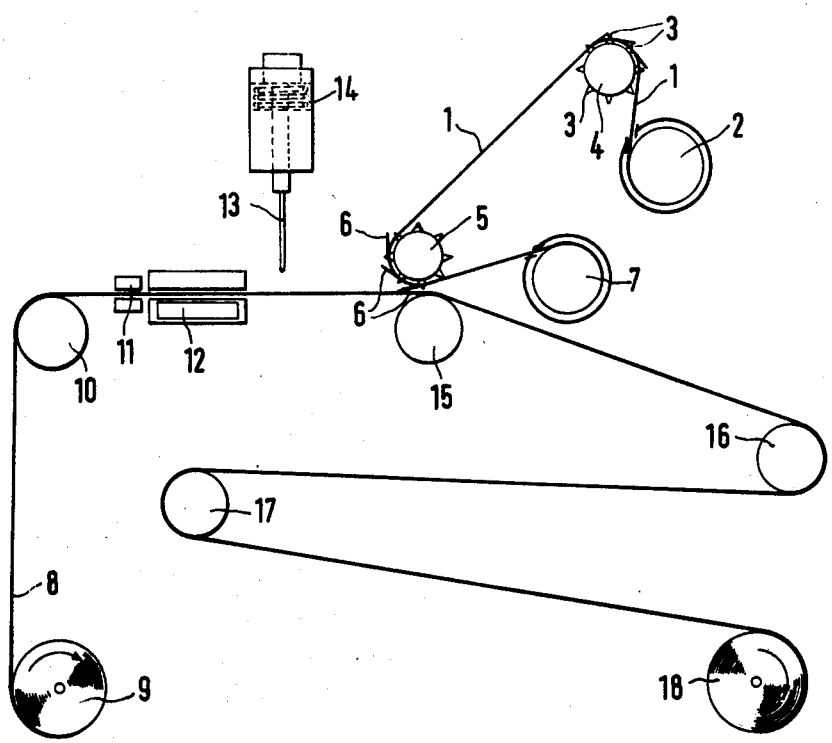

United States Patent [19]

Heanley et al.

[11] 4,137,866
[45] Feb. 6, 1979

[54] APPARATUS FOR PREPARATION OF BLOOD SAMPLES

[76] Inventors: Charles P. Heanley; Jozef K. Tylko; David G. S. Page, all of 5B Leachlade Rd., Faringdon, Oxon., England, SN7 8AJ

[21] Appl. No.: 785,111

[22] Filed: Apr. 6, 1977

[30] Foreign Application Priority Data

Apr. 9, 1976 [GB] United Kingdom ............... 14494/76

[51] Int. Cl.² ............................................. B05C 11/02
[52] U.S. Cl. .................................... 118/106; 195/127
[58] Field of Search ................ 118/106, 257, 14, 325; 195/127; 427/2; 23/253 R

[56] References Cited

U.S. PATENT DOCUMENTS

| 3,129,144 | 4/1964 | Page et al. ........................... 195/127 |
| 3,995,022 | 11/1976 | Heanley et al. ................. 118/100 X |
| 4,027,623 | 6/1977 | Adler ............................... 118/257 X |

*Primary Examiner*—John McIntosh
*Attorney, Agent, or Firm*—Dennison, Dennison, Meserole & Pollack

[57] ABSTRACT

Forming a blood trace of predetermined length and width on a flexible supporting strip by depositing a blood sample on the strip, contacting the sample with a trace tip carried by an adjacent strip and moving the sample relative to the tip through a predetermined course to control the width and length of said trace.

1 Claim, 3 Drawing Figures

U.S. Patent

Feb. 6, 1979

4,137,866

APPARATUS FOR PREPARATION OF BLOOD SAMPLES

This invention relates to the laying of traces of liquids and suspensions in general and in particular to the laying of traces of peripheral blood. Such traces can be prepared in a variety of ways. For instance, it is possible to have them drawn on a suitable substrate with pens of different type or by means of fine capillaries. Notably, Rubens Alves Pequeno in American Journal of Clinical Pathology teaches a "Simple Pen Method for Preparing Linear Blood Films for Accurate Differential Leukocyte Counts" in Volume 34, Number 6, pages 565 et seq. of the said Journal. W. Schiller in the U.S. Pat. No. 1,858,308 entitled: "Apparatus for the Preparation of Films of Blood" of 17th May, 1932, provides yet another method which involves certain degree of automation. The use of glass ribbon as a substrate carrying various physiological preparations is mentioned by H. P. Mansberg and J. Kusnetz in the Journal of Histochemistry and Cytology, Volume 14, Number 3, pages 260 et seq., under the title: Quantitative Fluorescence Microscopy, while the "Preparation of Stained Blood Films Using a Plastic Strip" has been given by Ronald D. Mackenzie in the Journal of Medical Laboratory Technology, 1962, Volume 19, page 184. Writing upon flexible films for the purpose of preparation of specimens for microscopic examination is also the subject of British Patent specification Number 1,036,776. Two of the co-inventors of the present invention Heanley and Tylko have also contributed to the prior art in this field namely: C. P. Heanley: "Tetronics Trace Laying System", Proceedings of 2nd Tenovus Symposium, Cardiff, 24th-25th October, 1968: J. K. Tylko: "Cytotopological Parameters their Measurements and Significance" ibid,; and Dawson, I. M. P.; Heanley, C. P., Heber-Percy, A. C., Tylko, J. K. Jour. Clin. Path., 20, 724, (1967): U.S. Pat. No. 3,995,022.

The general idea behind all the above techniques is the same namely to replace the tedious and often inaccurate manual methods of spreading blood on microscopic slides. Not only do such methods involve lengthy and often inaccurate raster type of scanning but they can also present certain infection hazards. However, hitherto attempts at producing automatically blood traces in the form of highly regular and narrow deposits which could be then fixed, stained and viewed met with rather limited success. Where hand held drawing pens or mapping pens were used, the drawing itself required great skill and did not give uniformly high quality. Above all such manual methods did not save time no did they provide much sought after standardisation. Where capillaries were tried the resulting traces were irregular and frequent differences in bulk physical properties between blood samples made the use of such devices limited. There were frequent clogging, selective depositions and a potential danger of cross-contamination where one and the same capillary or pen was repeatedly used and its washing imperfect. In the laying stage a fixed number of pins and spreaders were brought in turn into their respective trace forming positions and washing and drying stations. While it is possible to lay good blood traces with the above apparatus it was rapidly realised that the repeated use of the same spreaders create many problems. Firstly, there is always however small, the potential danger of transferring inadvertently some cells from the previous samples to the new ones by virtue of imperfect washing. Secondly, the washing and drying operations in order to be efficient require considerable complexity, time to accomplish and additional services such as jets of washing liquids and warm air. Thirdly, the mechanics of taking the spreaders out for washing and drying and bringing them with a high degree of precision back into the trace laying position introduces further costly complications and imposes the need for frequent servicing. As the system of preparing blood traces and subjecting them to a microscopic examination is intended essentially for routine haematological laboratory use, an alternative solution was sought and found in the present invention.

As will be shown, the present invention overcomes all of the above difficulties and provides in contrast to the previous art an apparatus that is simple, efficient and reliable in operation, eliminates the danger of inadvertent transfer of cells from one sample to another and yet can be compact enough to be when required carried to the patient. Equally, the operation of the apparatus is extremely simple and uniformly good results are obtained without any demand on dexterity of the operator.

It is therefore an object of the present invention to provide a method and apparatus for the preparation of peripheral blood traces upon flexible supporting strip suitable for microscopical examination.

It is a further object of the invention to provide a highly automated means for the preparation of blood traces, the said traces being all of controlled width and length.

It is yet a further object of the invention to eliminate in the said blood traces any possibility of cross contamination of any of the blood traces with matter derived from other traces and furthermore greatly reduce the potential danger of exposing operatives to certain blood-borne infections.

According to the invention the method of laying traces of peripheral blood comprises the steps of: depositing discrete drop of blood from depositing member upon flexible strip bringing said drop of blood upon said substrate into contact with a tip of trace laying member derived and protruding from another flexible strip and moving axially said drop of blood on said substrate so as to lay a predetermined length of blood trace; removing the said trace laying member from the trace laying position and bringing into the trace laying position the next trace laying member.

Thus the invention provides two flexible supports or strips: one upon which a discrete drop of blood is deposited and which serves and is henceforth referred to as the trace supporting base and the other, in which a plurality of trace laying members is punched axially at equal intervals and which, when flexed over a sprocketted pulley projects the said trace laying members along their planes tangent at their points of attachment to the said flexible support. The two flexible strips are so spatially disposed that during the movement of the trace supporting strip there is always a stationary trace laying member protruding downward towards the trace supporting strip to such extent that it will engage the deposited drop of blood when the said drop shall travel thereunder and thus form and support an index of blood contained between the said travelling trace supporting strip and the facing it plane of the said stationary trace laying member from which blood trace is formed and deposited upon the said trace supporting strip until the supply of blood is exhausted.

One way of automating the trace laying operations of the invention is to simultaneously with the deposition of blood drop start a sequence of operations which will firstly advance the trace laying member to its trace laying position and then actuate the transport of the trace supporting strip so as to produce the blood trace, stopping the transport of the said trace supporting strip at a prearranged, fixed distance after the supply of blood has been exhausted.

Conveniently, though not limiting the scope of the present invention, synchronisation of the trace laying member flexible support with the trace supporting base may be achieved by positioning a given trace laying member by means of a large diameter detent wheel. It is further particularly convenient for this purpose to employ a standard double perforated strip, e.g. a 16mm film base making the detent positions coincide with the eight sprocket index teeths of the pulley carrying the punched trace laying members in their flexible support. In this way, at a signal from the control circuitry the detent wheel and index sprocket are moved together until the next detent position is reached, thus providing high degree of precision.

The invention will now be described with reference to FIGS. 1, 2 and 3 in which

Figure 2:
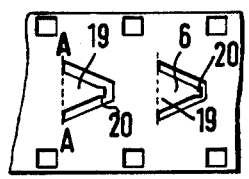
Figure 3:
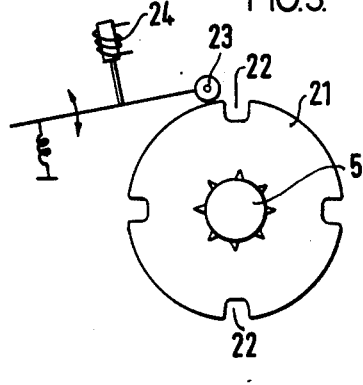

FIG. 1 shows the frontal elevation of a portable blood trace laying unit,

FIG. 2, a plan view of a portion of flexible strip with trace laying members and FIG. 3, a frontal elevation of a detent wheel.

In FIG. 1, the flexible strip with punched trace laying members 1, is stored in coreless cylindrical magazine 2, from which it is fed over the sprockets 3, of the pulley 4, to a similar pulley 5. As the strip is flexed over the pulley 5, the punched trace laying members 6, are shown to accept tangential positions. From pulley 5, the strip 1, with its used up trace laying members 6, is fed to the take-up spool 7. A trace supporting base 8, is wound on a spool 9, from which it passes over the roller 10, through a sensor station 11 and trace number display window 12. Different types of trace sensing and trace number displays may be used but one of the most convenient methods is to detect optically the presence of punched holes using a beam of polarised light and a suitable photoelectric detector. In this way, a control signal is derived from the trace carrying base at the start of each new trace. It is also convenient to punch out or otherwise mark on the trace supporting base trace numbers corresponding to each length of the trace prior to the laying of the traces. The trace numbers can be displayed in window 12. Downstream of the trace number display window 12, and directly above the trace supporting base is the blood applicator 13, in its mounting 14. In a portable blood trace laying unit a small amount of blood is collected on the tip of the blood applicator 12, and the applicator placed in its mounting 14. The applicator locating mount 14, also carries an actuating switch (not shown) which upon depressing the applicator in order to deposit a drop of blood does start the sequence of operations leading to the deposition of the blood trace. As the blood trace is laid at the protruding trace laying member 6, the trace supporting base 8, is supported accurately and firmly against the roller 15. Therefrom, the trace supporting base 8, with the deposited upon it blood trace travels over the rollers 16 and 17 to arrive in a dry state on the take-up spool 18.

FIG. 2, shows a plan view of a portion of the flexible strip 1, with the trace laying members 6, spaced axially at uniform intervals. Member 6, which during its passage over the pulley shall protrude tangentially along the dotted line marked "A — A", comprises two portions: a larger, regular trapesium shape 19, with its base at the dotted line "A — A", and a very small rectangular portion 20, at the tip of the protruding extremity. It is the width of the rectangular member 20, that relates to the ultimate width of the blood trace produced. As a rule blood traces of 250–1000 microns width are preferred, but where required, this range may be greatly increased by increasing the width of the rectangular member 20. In FIG. 3, the detent wheel 21 with peripherally equispaced indentations 22 engaging a roller 23, is placed axially with the sprocketted wheel 5. Roller 23, is raised out from the indentation 22, with the help of a solenoidal actuator 24. It also falls within the scope of the invention to provide means for preparing both flexible supports, by punching the necessary location holes, incorporating trace numbers and also punching the trace laying members.

It shall also be understood that certain modifications and improvements closely related to this art of laying blood traces may also fall within the compass of this invention and in particular alternative means for providing and detecting signals, energising and synchronising the sequences involved, introduction of various tensioning devices and coupling means in order to maintain the required accuracy as well as means for precision alignment, particularly between the pulleys 4 and 5.

What we claim is:

1. An apparatus for the laying of traces of peripheral blood comprising: a flexible strip and means for depositing a discrete drop of blood upon it; another flexible strip in which a plurality of trace laying members is punched axially at equal intervals and which when flexed over a sprocketed pulley projects the said trace laying members one at a time; means for disposing spatially the two flexible strips so that during the movement of the trace supporting strip there is always a stationary trace laying member protruding downward towards the trace supporting strip so that it will engage the deposited drop of blood when the said drop shall travel thereunder; forming and supporting an index of blood contained between the said travelling trace supporting strip and the facing it plane of the said stationary trace laying member thereby depositing upon the said trace supporting strip a blood trace.

* * * * *